US011206845B2

(12) United States Patent
Saini et al.

(10) Patent No.: US 11,206,845 B2
(45) Date of Patent: Dec. 28, 2021

(54) REDUCING MICROBIOLOGICAL CONTAMINATION DURING CHEESE MANUFACTURING PROCESS

(71) Applicant: WTI, Inc., Jefferson, GA (US)

(72) Inventors: Jasdeep K. Saini, Jefferson, GA (US); James L. Marsden, Jefferson, GA (US); Wolfgang P. Ludwig, Jefferson, GA (US)

(73) Assignee: WTI, INC., Jefferson, GA (US)

( * ) Notice: Subject to any disclaimer, the term of this patent is extended or adjusted under 35 U.S.C. 154(b) by 0 days.

(21) Appl. No.: 15/293,934

(22) Filed: Oct. 14, 2016

(65) Prior Publication Data

US 2017/0105425 A1    Apr. 20, 2017

Related U.S. Application Data

(60) Provisional application No. 62/242,621, filed on Oct. 16, 2015.

(51) Int. Cl.
| | |
|---|---|
| A23C 19/11 | (2006.01) |
| A23C 19/10 | (2006.01) |
| A23C 19/09 | (2006.01) |
| C12J 1/00 | (2006.01) |
| C12P 7/54 | (2006.01) |

(52) U.S. Cl.
CPC .............. *A23C 19/10* (2013.01); *A23C 19/09* (2013.01); *A23C 19/11* (2013.01); *A23V 2002/00* (2013.01); *C12J 1/00* (2013.01); *C12P 7/54* (2013.01)

(58) Field of Classification Search
CPC ......... A23C 19/09; A23C 19/10; A23C 19/11; C12J 1/00; C12P 7/54

USPC .................................................. 426/491, 334
See application file for complete search history.

(56) References Cited

U.S. PATENT DOCUMENTS

| | | | | |
|---|---|---|---|---|
| 2,141,698 | A * | 12/1938 | Saunders ............... | A23C 19/05 426/36 |
| 2010/0310738 | A1 * | 12/2010 | Ludwig .................. | A23B 4/027 426/266 |
| 2013/0189414 | A1 * | 7/2013 | Matsui ............... | A23C 19/0455 426/491 |
| 2015/0225683 | A1 * | 8/2015 | Boerefijn .............. | A23L 3/3463 426/321 |
| 2016/0227797 | A1 * | 8/2016 | Saini ....................... | A23B 4/12 |

OTHER PUBLICATIONS

NPL Jones AN (2002): in The Physics factbook Edited by Glenn Elert pp. 1-2.*

* cited by examiner

*Primary Examiner* — Bhaskar Mukhopadhyay
(74) *Attorney, Agent, or Firm* — Johnson, Marcou, Isaacs & Nix, LLC; F. Brent Nix, Esq.; Rachel D. Rutledge, Esq.

(57) ABSTRACT

Embodiments disclosed herein provide methods for reducing microbiological contamination during the cheese making process. Inhibition of microbial outgrowth is achieved by introducing an inhibitor at low concentration during the cheese making process. The inhibitor composition inhibits microbial outgrowth of pathogenic microbes associated with the cheese making process and controls and/or eliminates spoilage microorganisms to prolong shelf-life and maintain quality of the final cheese product. The inhibitor composition may be added to the milk prior to curd formation, after curd formation but prior to setting, or both. The inhibitor composition may be used with both pasteurized and unpasteurized cheeses.

19 Claims, 1 Drawing Sheet

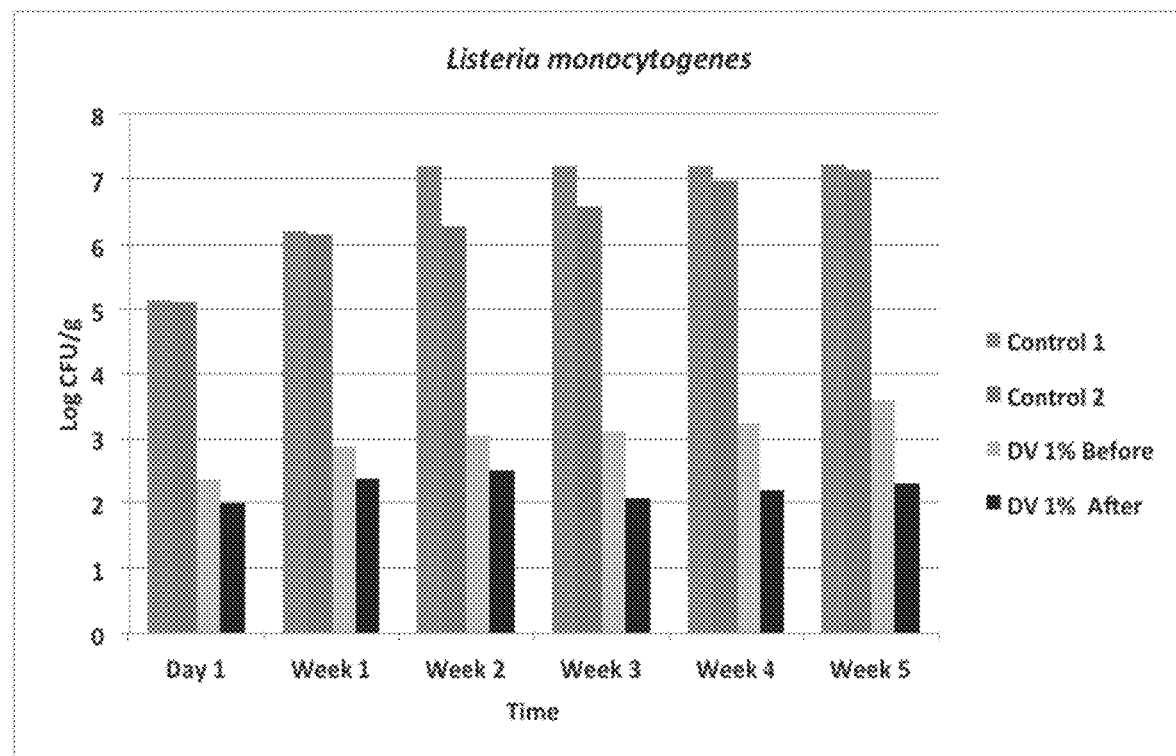

REDUCING MICROBIOLOGICAL CONTAMINATION DURING CHEESE MANUFACTURING PROCESS

CROSS-REFERENCE TO RELATED APPLICATIONS

This patent application claims priority to U.S. Provisional Patent Application No. 62/242,621, filed Oct. 16, 2015, and entitled "Reducing Microbiological Contamination During Cheese Manufacturing Process." The entire disclosure of the above-identified priority application is hereby fully incorporated herein by reference.

TECHNICAL FIELD

The invention relates to methods for reducing microbiological contamination during the cheese manufacturing process thereby improving safety and increasing the shelf life of the resulting cheese product.

BACKGROUND

The ambient conditions during the cheese manufacturing process provide an ideal environment that supports the growth of microorganisms and allows for cross contamination in the cheese products produced. In addition, certain microbes such as *Listeria monocytogenes* further pose a unique problem being an environmental contaminant that is ubiquitous in nature and able to grow and multiple even under cold storage conditions. Accordingly, there is a need in the art for microbial inhibitors that inhibit the growth of pathogenic microbes as well as other microbes that lead to cheese spoilage. However, an inhibitor must not negatively impact the commercial properties of the cheese and remain entirely safe for human consumption.

SUMMARY

In one aspect, the embodiments described herein are directed to methods for inhibiting or reducing biological contamination and outgrowth in cheese products comprising adding an inhibitor composition in low concentration during the cheese manufacturing process. In certain example embodiments, the inhibitor composition comprises dried buffered vinegar. In certain other example embodiments, the inhibitor composition consists only of dried buffered vinegar. The inhibitor composition may be added at a concentration of between 0.1% to 5% w/v. In certain example embodiments the inhibitor composition may be added at a concentration between approximately 0.25% and approximately 1% w/v. The inhibitor composition may have pH of between 5.0 and 6.5. In certain example embodiments, the inhibitor composition may have a pH of between approximately 5.9 to approximately 6.1.

The inhibitor composition may be added at multiple points during the cheese manufacturing process. In certain example embodiments, the inhibitor composition may be added to the milk. In certain other example embodiments, the inhibitor composition may be added to the curds after formation but prior to setting. In certain other example embodiments, the inhibitor composition may be added to both the milk and to the curds after formation but prior to setting.

The inhibitor composition may be used to inhibit microbial outgrowth and contamination in a wide variety of cheeses including, but not limited to, raw milk cheeses, fresh cheeses, soft-ripened cheeses, washed-rind cheeses, semi-soft cheeses, semi-hard cheeses, hard cheeses, blue-veined cheeses, double or triple crème cheeses, processed cheeses or, pasta filata cheeses.

The inhibitor composition may be used to inhibit microbial outgrowth and contamination of bacteria and fungi, including molds and yeasts. In certain example embodiments, the inhibitor composition inhibits bacterial growth. In certain other example embodiments, the inhibitor composition inhibits fungal growth, including yeasts and molds. In certain other example embodiments, the inhibitor composition can inhibit a combination of bacteria and fungi, including yeast and molds.

These and other aspects, objects, features, and advantages of the example embodiments will become apparent to those having ordinary skill in the art upon consideration of the following detailed description of the illustrated example embodiments.

BRIEF DESCRIPTION OF THE DRAWINGS

FIG. 1 is a bar graph showing the levels of *Listeria monocytogenes* recovered from raw milk cheese during a five week treatment with inhibitor compositions in accordance with certain example embodiments.

DETAILED DESCRIPTION OF THE EXAMPLE EMBODIMENTS

Overview

Embodiments disclosed herein represent methods for reducing microbiological contamination during the cheese making process. Inhibition of microbial outgrowth is achieved by introducing an inhibitor at low concentration during the cheese making process. The inhibitor composition inhibits microbial outgrowth of pathogenic microbes associated with the cheese making process and controls and/or eliminates spoilage microorganisms to prolong shelf-life and maintain quality of the final cheese product. The inhibitor may be added to the milk prior to curd formation, after curd formation but prior to setting, or both. The inhibitor composition may be used with both pasteurized and un-pasteurized cheeses.

In certain example embodiments, the inhibitor composition comprises dried buffered vinegar. In certain other example embodiments, the inhibitor composition consists only of dried buffered vinegar. The dried buffered vinegar may comprise acetic acid and its consumable salt, such as but not limited to, sodium acetate. Source vinegar materials may include, for example, corn, sugar cane, glacial acetic, and apple cider. In certain example embodiments, the dried buffered vinegar comprises 1-12% acetic acid. In certain other example embodiments, the dried buffered vinegar comprises 4-8% acetic acid. The dried buffered vinegar may be prepared using standard buffering agents known in the art. An example buffered dried vinegar is WTI DV® available from WTI Inc. (Jefferson, Ga.).

In certain example embodiments, the buffered dried vinegar composition may have a pH value of approximately 5.0 to approximately 6.5. In certain other example embodiments, the pH of the dried buffered vinegar is approximately 5.0 to approximately 6.4, approximately 5.0 to approximately 6.3, approximately 5.0 to approximately 6.2, approximately 5.0 to approximately 6.1, approximately 5.0 to approximately 6.0, approximately 5.0 to approximately 5.9, approximately 5.0 to approximately 5.8, approximately 5.0 to approximately 5.7, approximately 5.0 to approximately 5.6, approximately 5.0 to approximately 5.5, approximately 5.0 to approximately 5.4, approximately 5.0 to approximately 5.3, approximately 5.0 to approximately 5.2, or approximately 5.0 to approximately 5.1. In certain other example embodiments, the pH of the dried buffered vinegar is between approximately 5.4 to approximately 6.3, approximately 5.4 to approximately 6.2, approximately 5.4 to approximately 6.1, approximately 5.4 to approximately 6.0, approximately 5.4 to approximately 5.9, approximately 5.4 to approximately 5.8, approximately 5.0 to approximately 5.7, approximately 5.4 to approximately 5.6, or approximately 5.4 to approximately 5.5. In certain other example embodiments, the pH of the dried buffered vinegar is approximately 5.9 to approximately 6.1. As used in the context of describing pH value ranges above, "approximately" means a pH value within 0.05 of the stated pH values.

In certain example embodiments, the inhibitor composition is added in an effective amount to the milk used to start the cheese manufacturing process. In another example embodiment, the buffered dried vinegar composition is added in an effective amount after curd formation but prior to setting. In certain other example embodiments, it may be added to both the milk and after curd formation but prior to setting. The two applications may be made at equal concentrations. In some embodiments, the first application may be made at a higher concentration than the second application. In certain other embodiments, the first application may be at a lower application than the second application. An effective amount as used herein refers to a concentration of the inhibitor composition that is sufficient to inhibit microbial growth without adversely affecting the taste, firmness, color, or other commercial features of the final cheese product. Inhibition of microbial growth as used herein refers to partial or complete inhibition that results in an increased lag phase, or a measured outgrowth of less than 2 log CFU/g of pathogenic microorganisms such as *Listeria monocytogenes* throughout the shelf-life of the product. As used herein, shelf-life refers to standard definitions of cheese product shelf-life known in the art and may be characterized by organoleptic changes, chemical changes, microbial growth of certain other microbial indicators, or a combination thereof.

The inhibitor composition may be added to the raw milk or to the cheese curds after formation but prior to setting at a concentration of approximately 0.1% to approximately 5% w/v. In certain example embodiments, the inhibitor composition is at a concentration of approximately 0.1% to approximately 4%, approximately 0.1% to approximately 3%, approximately 0.1% to approximately 2%, between approximately 0.1% to approximately 2%, between approximately 0.1% to approximately 1%. In certain other example embodiments, the inhibitor composition is at a concentration of approximately 0.25% to approximately 5%, approximately 0.25% to approximately 4%, approximately 0.25% to approximately 3%, approximately 0.25% to 2%, approximately 0.25% to 1%, or approximately 0.25% to approximately 0.5%. In another example embodiment, the inhibitor composition is at a concentration of approximately 0.5% to approximately 5%, approximately 0.5% to approximately 4%, approximately 0.5% to approximately 3%, approximately 0.5% to approximately 2%, or approximately 0.5% to approximately 1%. In another example embodiment, the inhibitor composition is at a concentration of approximately 0.75% to approximately 5%, approximately 0.75% to approximately 4%, approximately 0.75% to approximately 3%, approximately 0.75% to approximately 2%, or approximately 0.75% to 1%. In another example embodiment, the inhibitor composition is at a concentration of approximately 1% to approximately 5%, approximately 1% to approximately 4%, approximately 1% to approximately 3%, or approximately 1% to approximately 2%. In another example embodiment, the inhibitor composition is at a concentration of approximately 0.1% to approximately 0.25%, approximately 0.25% to approximately 0.5%, approximately 0.25% to approximately 0.75%, or approximately 0.5% to approximately 0.75%. All concentrations of the inhibitor composition as recited in this paragraph are given as weight percent volume (w/v). As used in the context of describing the concentration of the inhibitor composition, "approximately" means a concentration value within 0.05% w/v of the stated concentrations.

The inhibitor compositions described herein may be used to prevent microbial outgrowth in the manufacturing and processing of a variety of different cheeses. The cheese may be pasteurized or un-pasteurized. Cheese types with which the inhibitor compositions may be used include, but are not limited to, raw milk cheeses, fresh cheeses, soft-ripened cheeses, washed-rind cheeses, semi-soft cheeses, semi-hard cheeses, hard cheeses, blue-veined cheeses, double or triple crème cheeses, processed cheeses, and pasta filata cheeses.

The inhibitor compositions described herein may be used to inhibit microbial outgrowth from one or more microbes. The microbe may be a pathogenic microbe or a microbe that otherwise adversely effects the taste, odor, color, consistency or other commercial properties of the cheese product. In certain example embodiments, the microbe is a bacteria. The bacteria may be a psychrotroph, a coliform, a lactic acid bacteria, or a spore-forming bacteria. In certain example embodiments, the bacteria is a *Stapylococcus* species, a *Pseudomonas* species, a *Micrococcus* species, an *Aerococcus* species, a *Lactococcus* species, a *Leuconostoc* species, a *Streptococcus* species, a *Bacillus* species, a *Clostridium* species, a *Eubacteria* species, an *Enterococcus* species, a *Listeria* species, or a combination thereof. In certain example embodiments, the bacteria is a *Listeria* species. In certain example embodiments, the *Listeria* species is *L. monocytogenes*.

In certain example embodiments, the microbe is a fungi. In certain example embodiments, the fungi is a yeast. Example yeast may include, but are not limited to, an *Aspergillus* species, a *Geotrichum* species, a *Saccharomyces* species, a *Hansenula* species, a *Candida* species, a *Kluyveromyces* species, a *Debaryomyces* species, a *Pichia* species, or combination thereof. In certain example embodiments, the fungi is a mold. Example molds include, but are not limited to, a *Penicillium* species, a *Cladosporium* species, a *Byssochlamys* species, or a combination thereof.

The methods described herein may be used to inhibit microbial outgrowth for at least 4 weeks, at least 5 weeks, at least 6 weeks, at least 7 weeks, or at least 8 weeks for a un-pasteurized cheese. The methods described herein may be used to inhibit microbial outgrowth for at least 2 months, at least 3 months, at least 4 months, at least 5 months, at least 6 months, at least 7 months, at least 8 months, at least 9 months, at least 10 months, at least 11 months, or at least 12 months for a pasteurized cheese.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Efficacy of Inhibitor Compositions in Controlling *Listeria Monocytogenes* in Raw Milk Cheese A five-strain cocktail of *Listeria monocytogenes* was used for inoculation of samples. Cultures were obtained from American Type Culture Collection (ATCC). For inoculum preparation, freeze-dried cultures were grown in Tryptic Soy Broth (TSB) and fresh overnight 24 hour grown cultures were used. Each strain was combined into a single mixed culture suspension to obtain the five-strain cocktail. The cell density of the inoculum was determined by spread plating and incubating the plates at 35° C. for 24 hours. The target inoculum level for the study was 4-5 log CFU/g.

The five-strain cocktail of *L. monocytogenes* was added to raw milk to a target inoculum level of 5 log CFU/g after a temperature of 32° C. was reached.

A one gallon batch of raw milk was used for each experimental set. The temperature of the mix was raised to approximately 30 to 33° C. Bacterial culture and the treatment were then added. The milk was set by adding rennet at 0.01% and allowing the curd to form for 30 mins. Cheese knives that produced ½ inch cubes were used to cut the curds. After cutting, curds were stirred for one hour and the temperature was raised to 35° C. Whey was then drained and about 50% of the original volume and curds were salted at 2%. Curds were then molded and allowed to drain for one hour. The resulting cheese was bagged and vacuum packaged for five week storage at refrigeration temperatures.

The treatments were applied at two different stages, in raw milk and post rennet addition to determine the best point of application. After the treatment application, the cheese samples were packaged into polypropylene bags under vacuum and stored at refrigerated temperatures for 5 weeks.

Duplicate samples were pulled at Day 1, week 1, 2, 3, 4, and 5. A 25 g sample was suspended in 75 g buffered peptone water, stomached for a min, and spread plated on to modified oxford medium for *L. monocytogenes* enumeration. Plates were incubated at 35° C. for 24-48 h. Additionally samples were also plated on de Mann Rogosa Sharpe (MRS) agar to determine lactic acid bacteria counts and MacConkey Sorbitol (MSA) agar to determine coliform count during the shelf life of the test.

FIG. 1 shows *Listeria monocytogenes* counts in raw milk cheese treated with dried buffered vinegar (DV). In this treatment, the bacteria started to proliferate only after 3 weeks. Additionally, no significant differences were seen between the bacterial numbers from treatments that were added to the raw milk in comparison to treatments that were added post rennet addition. The lactic acid bacteria numbers (Table 1) showed 1-1.5 log CFU/g increase during the 5 week test for treated samples while in control samples the lactic acid bacteria increased close to 3 log CFU/g. The coliform count (Table 2) reduced to below 40 CFU/g (detection limit) in one week in all of the samples.

TABLE 1

Lactic Acid bacteria in raw milk cheese during 5 week treatment with dried buffered vinegar

| Sample | Day 1 | Week 1 | Week 2 | Week 3 | Week 4 | Week 5 |
|---|---|---|---|---|---|---|
| Control 1 | 4.39 | 4.4 | 5.82 | 6.28 | 6.49 | 7.26 |
| Control 2 | 4.1 | 4.22 | 5.94 | 6.35 | 6.58 | 6.96 |
| DV 1% Before | 4.32 | 4.35 | 5.42 | 5.57 | 5.71 | 5.8 |
| DV 1% After | 4.3 | 4.3 | 4.8 | 5.09 | 4.98 | 4.92 |

TABLE 2

Coliform count in raw milk cheese during 5 week treatment with dried buffered vinegar

| Sample | Day 1 | Week 1 | Week 2 | Week 3 | Week 4 | Week 5 |
|---|---|---|---|---|---|---|
| Control 1 | 3.11 | <40 cfu/g | <40 cfu/g | <40 cfu/g | <40 cfu/g | <40 cfu/g |
| Control 2 | 3.08 | <40 cfu/g | <40 cfu/g | <40 cfu/g | <40 cfu/g | <40 cfu/g |
| DV 1% Before | 1.6 | <40 cfu/g | <40 cfu/g | <40 cfu/g | <40 cfu/g | <40 cfu/g |
| DV 1% After | 1.9 | <40 cfu/g | <40 cfu/g | <40 cfu/g | <40 cfu/g | <40 cfu/g |

What is claimed is:

1. A method to reduce microbiological contamination during cheese processing consisting of adding a dried buffered vinegar composition to a cheese precursor during a cheese manufacturing process in an effective amount to inhibit growth by a microbe; wherein the dried buffered vinegar has a concentration of approximately 0.25% to approximately 1.25% (w/v) and a pH of approximately 5.4 to approximately 6.3.

2. The method of claim 1, wherein the dried buffered vinegar has a pH of approximately 5.9 to approximately 6.1.

3. The method of claim 1, wherein the dried buffered vinegar is added to a milk prior to curd formation.

4. The method of claim 1, wherein the dried buffered vinegar is added after curd formation but prior to setting.

5. The method of claim 1, wherein the microbe is a bacterium or a fungus.

6. The method of claim 5, wherein the bacterium is a psychrotroph, a coliform, a lactic acid bacterium, or a spore-forming bacterium.

7. The method of claim 5, wherein the bacterium is a *Pseudomonas* species, a *Micrococcus* species, an *Aerococcus* species, a *Lactococcus* species, *Leuconostoc* species, a *Streptococcus* species, a *Bacillus* species, a *Clostridium* species, a *Eubacterium* species, an *Enterococcus* species, or a *Listeria* species.

8. The method of claim 7, wherein the bacterium is a *Listeria* species.

9. The method of claim 8, wherein the bacterium is *L. monocytogenes*.

10. The method of claim 5, wherein the fungus is a yeast.

11. The method of claim 10, wherein the yeast is an *Aspergillus* species, a *Geotrichum* species, a *Saccharomyces* species, a *Hansenula* species, a *Candida* species, a *Kluyveromyces* species, a *Debaryomyces* species, or a *Pichia* species.

12. The method of claim 5, wherein the fungus is a mold.

13. The method of claim 12, wherein the mold is a *Penicillium* species, a *Cladosporium* species, or a *Byssochlamys* species.

14. The method of claim 1, where the cheese is a raw milk cheese or an aged cheese.

15. The method of claim 1, wherein the cheese is a fresh cheese, a soft-ripened cheese, a washed-rind cheese, a semi-soft cheese, a semi-hard cheese, a hard cheese, a blue-veined cheesed, a double or triple crème cheese, a processed cheese, or a pasta filata cheese.

16. The method of claim 1, wherein microbiological contamination is inhibited for at least four weeks.

17. The method of claim 1, wherein the microbiological growth is inhibited for at least 6 months.

18. The method of claim 1, wherein the cheese precursor is raw milk.

19. The method of claim 1, wherein the dried buffered vinegar is added both to raw milk and after curd formation.

* * * * *

UNITED STATES PATENT AND TRADEMARK OFFICE
CERTIFICATE OF CORRECTION

PATENT NO. : 11,206,845 B2
APPLICATION NO. : 15/293934
DATED : December 28, 2021
INVENTOR(S) : Jasdeep K. Saini, James L. Marsden and Wolfgang P. Ludwig Page 1 of 1

It is certified that error appears in the above-identified patent and that said Letters Patent is hereby corrected as shown below:

In the Specification

Column No. 3, Line No. 39, "shelf-life" should be -- shelf life --
Column No. 4, Line No. 34, "Stapylococcus" should be -- Staphylococcus --
Column No. 5, Line Nos. 52-53, "de Mann Rogosa Sharpe (MRS)" should be -- de Man, Rogosa and Sharpe (MRS) --

Signed and Sealed this
Twenty-sixth Day of July, 2022

Katherine Kelly Vidal
*Director of the United States Patent and Trademark Office*